(12) United States Patent
Cogan et al.

(10) Patent No.: US 8,849,369 B2
(45) Date of Patent: Sep. 30, 2014

(54) WIRELESS RECORDING AND STIMULATION OF BRAIN ACTIVITY

(75) Inventors: Stuart F. Cogan, Sudbury, MA (US); Philip R. Troyk, Morton Grove, IL (US); John S. Ebersole, Chesterton, IN (US); Vernon L. Towle, Chicago, IL (US)

(73) Assignee: EIC Laboratories, Norwood, MA (US)

( * ) Notice: Subject to any disclaimer, the term of this patent is extended or adjusted under 35 U.S.C. 154(b) by 1206 days.

(21) Appl. No.: 12/687,675

(22) Filed: Jan. 14, 2010

(65) Prior Publication Data

US 2010/0198297 A1 Aug. 5, 2010

Related U.S. Application Data

(60) Provisional application No. 61/144,929, filed on Jan. 15, 2009.

(51) Int. Cl.
*A61B 5/0478* (2006.01)
*A61N 1/05* (2006.01)
*A61N 1/36* (2006.01)
*A61B 5/00* (2006.01)
*A61N 1/02* (2006.01)

(52) U.S. Cl.
CPC .......... *A61N 1/0531* (2013.01); *A61N 1/36082* (2013.01); *A61N 1/0504* (2013.01); *A61B 5/0006* (2013.01); *A61B 5/0478* (2013.01); *A61N 1/025* (2013.01); *A61B 2562/125* (2013.01); *A61B 5/4094* (2013.01); *A61B 5/0031* (2013.01); *A61N 1/36014* (2013.01)
USPC .......................... 600/378; 600/393; 607/116

(58) Field of Classification Search
CPC  A61N 1/37229; A61N 1/0531; A61N 1/0529
USPC ............ 600/372–373, 377–378, 393; 607/45, 607/115–117, 139, 148, 152
See application file for complete search history.

(56) References Cited

U.S. PATENT DOCUMENTS

| | | | | |
|---|---|---|---|---|
| 6,016,449 | A * | 1/2000 | Fischell et al. | 607/45 |
| 2003/0187490 | A1 * | 10/2003 | Gliner | 607/116 |
| 2006/0184209 | A1 * | 8/2006 | John et al. | 607/45 |
| 2009/0131995 | A1 * | 5/2009 | Sloan et al. | 607/3 |
| 2009/0149913 | A1 * | 6/2009 | Putz et al. | 607/45 |

* cited by examiner

*Primary Examiner* — Carl H Layno
*Assistant Examiner* — Jessica Anthony
(74) *Attorney, Agent, or Firm* — Novel IP

(57) ABSTRACT

Subdural arrays transmit electrocorticogram recordings wirelessly, across the patient's skull, allowing the craniotomy used for surgical placement of the arrays to be completely closed. In various embodiments, the arrays also respond to commands, applying signal patterns to the patient's brain for diagnostic and treatment purposes.

17 Claims, 11 Drawing Sheets

WIRELESS RECORDING AND STIMULATION OF BRAIN ACTIVITY

RELATED APPLICATION

The present application claims priority to and the benefits of U.S. Provisional Application Ser. No. 61/144,929, filed on Jan. 15, 2009, the entire disclosure of which is hereby incorporated by reference.

FIELD OF THE INVENTION

This invention relates to improved devices and methods for recording electrical brain activity for the purpose of identifying regions in the brain exhibiting abnormal electrical activity, and more particularly to the identification of regions in the brain that originate or spread seizures associated with epilepsy and other brain dysfunctions.

BACKGROUND

Surgical resection of epileptogenic foci is a commonly practiced and often beneficial treatment for patients suffering debilitating seizures arising from otherwise intractable epilepsy. The success of this procedure depends on the ability of the medical team to precisely locate the epileptogenic zones in the patient's brain and to identify important cortical regions, such as eloquent cortex, that must be avoided during resection. To map epileptogenic activity, a combination of non-invasive imaging (e.g., magnetic resonance imaging or computer-aided tomography) and scalp recordings may be combined with electrocorticogram (ECoG) recordings from electrodes placed subdurally on the surface of the brain. A one- to two-week period of recording with subdural electrode arrays remains the accepted best clinical practice for localizing epileptogenic zones for the purpose of surgical resection. The electrode arrays also facilitate electrical stimulation of the cortex to locate important functional regions that must be preserved.

In general, to adequately identify the location of epileptogenic foci, a number of seizure events are recorded and the patient remains tethered to the recording equipment during the monitoring period. It is common practice to implant several subdural arrays to record from a wide area of the surface of the brain, and patients will typically have many cables exiting their heads. This invasive surgical procedure has drawbacks, including: (a) a lengthy and costly hospital stay is required; (b) a family member or sitter must typically be with the patient at all times; (c) patients may have difficulty coping with the need to remain in bed and tethered to the wall by cables; (d) long duration implantations increase the likelihood of serious infection; (e) there is a risk of intracerebral hemorrhage if the cables are accidentally pulled and the grids move; and (f) 10-20% of patients do not have enough seizures during their hospitalization to identify the epileptic zone with certainty.

These disadvantages of ECoG monitoring stem from the use of subdural arrays that are wired directly from within the patient's skull to external recording and data storage equipment. The risk of infection, created by the cables exiting the patient's head and the prohibitive expense of prolonged hospitalization, are generally the principal factors that limit the duration of ECoG monitoring to 1-2 weeks. It is also clinical practice to shorten the length of hospitalization by inducing seizures with anti-epileptic drug withdrawal since the patient, even with medically intractable epilepsy, will be taking medication to control seizures. Withdrawing medication is often associated with a change in the type of seizure experienced by the patient. The patient's usual or habitual seizure pattern may be replaced by more severe convulsive seizures that place the patient at risk for seizure-related morbidities of bodily trauma, aspiration, and hypoxia, as well as potentially fatal cardiac arrhythmias or cardio-respiratory arrest.

Seizures associated with drug withdrawal are also more likely to be non-habitual (atypical) and begin in brain areas that are otherwise well-controlled by medications. The recording of atypical seizure activity can result in false localization information.

While the use of electromagnetic telemetry to transmit brain activity wirelessly and, in particular, for recording epileptogenic activity is known, critical to the clinical application of wireless ECoG recording is the ability to electrically stimulate the cortex to determine regions of the brain responsible for functions that must be preserved during resection. In prior-art clinical practice, electrodes on wired subdural recording arrays are connected to an electrical stimulator using direct-wired, external mechanical connectors, and different combinations of electrodes on the arrays are stimulated electrically, usually with a series of charge-balanced biphasic current pulses. The patient's response to the stimulation determines whether the cortex underlying the electrodes is responsible for function that must be preserved. Since it is important to locate these functional regions as precisely as possible, the electrical stimulation is usually applied as a bipolar pulse train between adjacent pairs of electrodes on the subdural array. It may be necessary to perform these functional studies at various times throughout the monitoring period. There is therefore a need for systems capable of providing electrical stimulation at the discretion of the medical team at appropriate times during the monitoring period.

SUMMARY OF THE INVENTION

In various embodiments, the present invention is directed to the use of subdural arrays that transmit ECoG recordings wirelessly. The ECoG waveforms are transmitted across the patient's skull, allowing the craniotomy used for surgical placement of the arrays to be completely closed. The patient may then wear a receiver incorporated into a skullcap, or similar headwear that collects the transmitted ECoG recordings. The receiver in the headwear is connected to external hardware that stores the recordings. The patient is then free to remove and replace the headwear for showering or other daily activities. Wireless ECoG recording has many advantages: (a) patients may be discharged from the hospital for the monitoring period, avoiding lengthy and costly hospitalization; (b) ECoG recordings can be obtained at home, where sitters are not necessary; (c) patients may move about freely; (d) because no cables enter the head, morbidity or mortality from infections is reduced; (e) elimination of transcutaneous cables minimizes or eliminates the risk of dislodging the implanted arrays; and (f) continuous recordings for many weeks or even months is possible, greatly increasing the probability of recording a higher number of seizures and improving the accuracy of the epileptogenic localization.

Wireless ECoG arrays in accordance with embodiments of the present invention avoid recording of atypical seizure activity, which can result in false localization information, and provide an improved approach to locating epileptogenic foci. Recording ECoG activity can take place when the patient is taking his or her normal (or substantially normal) anti-seizure medications, and the monitoring period can continue until sufficient habitual seizure activity is observed to identify the pharmacologically intractable epileptogenic foci.

This approach increases the accuracy of and confidence in the identification of epileptogenic zones and accordingly improves the outcome of epilepsy surgery.

Accordingly, in a first aspect, embodiments of the invention relate to an implantable medical device that comprises an array of electrodes for communicating with a subject's brain and control circuitry that communicates with the electrodes, i.e., sends electrical signals to the electrodes and receives electrical signals from the electrodes. The implantable medical device also includes wireless transmission circuitry that can respond to the control circuitry. The wireless transmission circuitry can transmit digital data, corresponding to the brain signals sensed by the electrodes, outside the site of implantation—i.e., outside the subject's skull. The implantable medical device also includes wireless receiver circuitry for receiving wireless commands from outside the site where the device is implanted. The control circuitry respond to these commands, and the electrodes, which may receive signals from the control circuitry, can provide an electrical stimulus to the subject's brain in accordance with the wireless commands received.

In some embodiments of the implantable medical device, the transmission circuitry can include means (e.g., one or more metal coils) that facilitate magnetic inductive coupling. The receiver circuitry, either alternatively or in addition to the transmission circuitry, may include means (e.g., one or more metal coils) that facilitate magnetic inductive coupling. For example, the same single coil can be used for transmission and reception.

The electrodes and the circuitry of the implantable medical device, in some embodiments, can be mounted on a substrate that comprises one or more layers of flexible polymer. The electrodes may be coated with iridium oxide. The medical device may additionally include metal conductors, disposed on the substrate, for connecting the circuitry and the electrodes. The substrate may further comprise more than one layer of flexible polymer and a film, which itself may comprise amorphous silicon carbide, amorphous silicon oxycarbide, or both. A film may be disposed between a substrate layer and the conductors. Alternatively or additionally, a film may be disposed between two substrate layers.

In a second aspect, embodiments of the invention relate to a method of brain monitoring and treatment. The method comprises subdurally implanting a device comprising an array of electrodes for communicating with a patient's brain. Electrodes communicating with a patient's brain can receive voltages or signals from the brain and/or apply stimuli voltages or currents to the brain. The method also includes causing wireless transmission of digital data corresponding to brain signals sensed by the electrodes, and transmitting wireless commands to cause the electrodes to provide an electrical stimulus to the patient's brain in accordance with the commands.

In a third aspect, embodiments of the invention relate to a method of monitoring brain signals. The method comprises the steps of implanting at least one wireless array subdurally in a patient and maintaining the patient on a normal regimen of anti-seizure medication. The method also includes wirelessly measuring, via the wireless array, the brain signals. These signals are measured for a period of time sufficient to record adequate habitual seizure activity to localize pharmacologically intractable epileptogenic foci.

In some embodiments the method may further comprise conducting cortical mapping studies via wireless communication with the wireless array. The wireless array, in response to the communication received, may cause electrical stimulation of the patient's brain.

In a fourth aspect, embodiments of the invention relate to a method of determining optimum stimulation parameters for suppressing epileptogenic seizures. The method comprises implanting at least one wireless array subdurally in a patient and maintaining the patient on a normal regimen of anti-seizure medication. The method additionally comprises causing wireless transmission of digital data corresponding to brain signals, which are sensed by the array. On the basis of the transmitted data, the onset of habitual seizures may be identified. The method also includes wirelessly causing the array to apply electrical stimulation signals at one or more electrode sites on the array. The sites to be selected and the magnitudes of the stimulation signals to be applied via electrodes at the selected sites are determined so as to treat the seizures.

Embodiments of the present invention involve a wireless subdural electrode array having a plurality of electrodes for recording electrical brain activity and for electrically stimulating the brain, wherein each electrode is capable of providing the recording or stimulation function. The recording function of the array may be managed by an electrical circuit either on or connected to the array and implanted within the cranium of the patient. The electrical circuit is desirably capable of autonomous operation, recording and transmitting ECoG waveforms via a wireless electromagnetic link whenever power is provided to the array. The same electrical circuit or a second electrical circuit, also implanted within the patient's cranium, can provide electrical stimulation pulses between electrodes on the array; the electrode selection, stimulus magnitude, frequency, duration and time of imposition of the stimulation may be controlled by the clinician via the wireless electromagnetic link. Power is provided to the subdural array and electrical circuit by a wireless electromagnetic link or by a power source connected to the array and located within the cranium of the patient. An advantage of certain embodiments of the invention, therefore, is the ability not only to record but to facilitate wireless electrical stimulation of the patient's brain in a manner that can be commanded wirelessly by the clinician.

LIST OF FIGURES

Figure 6:
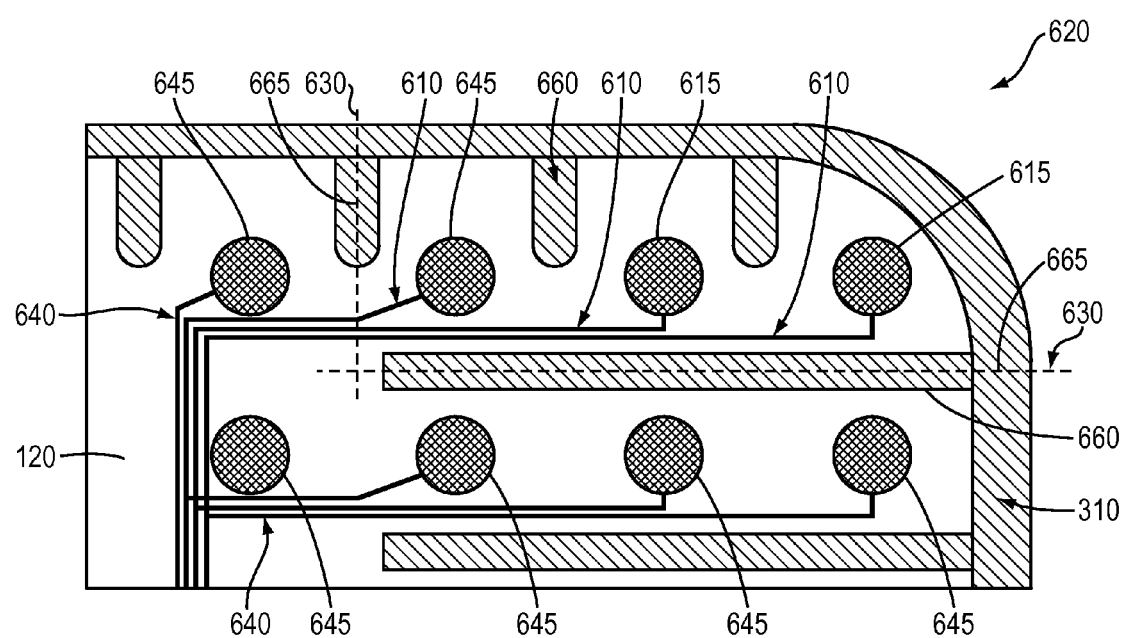

FIG. 6 schematically illustrates a portion of a subdural array showing a representative pattern of metal interconnects that permits selective removal of electrodes without impairing the function of other electrodes on the array.

Figure 7:
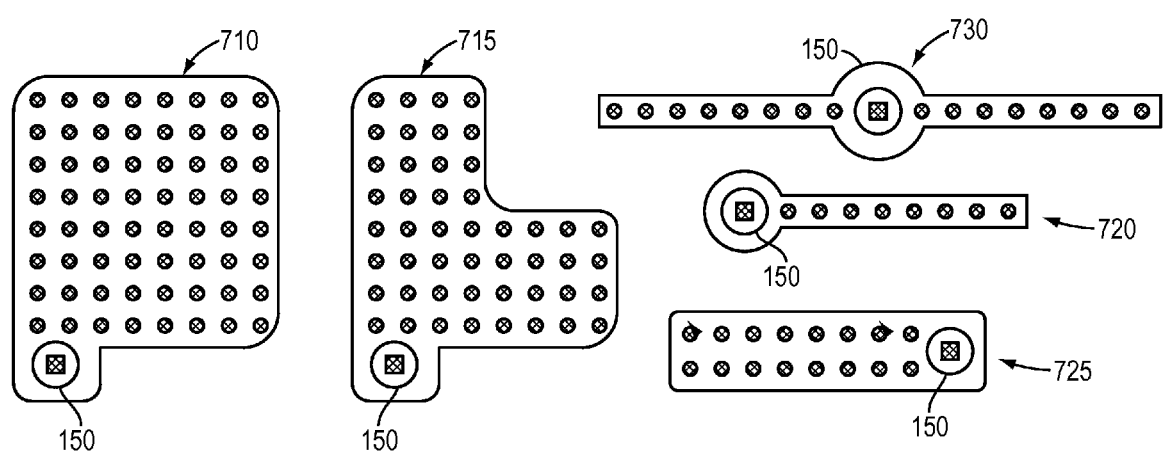

FIG. 7 schematically illustrates representative examples of subdural wireless arrays with different numbers of electrode sites arranged in different configurations.

Figure 8:
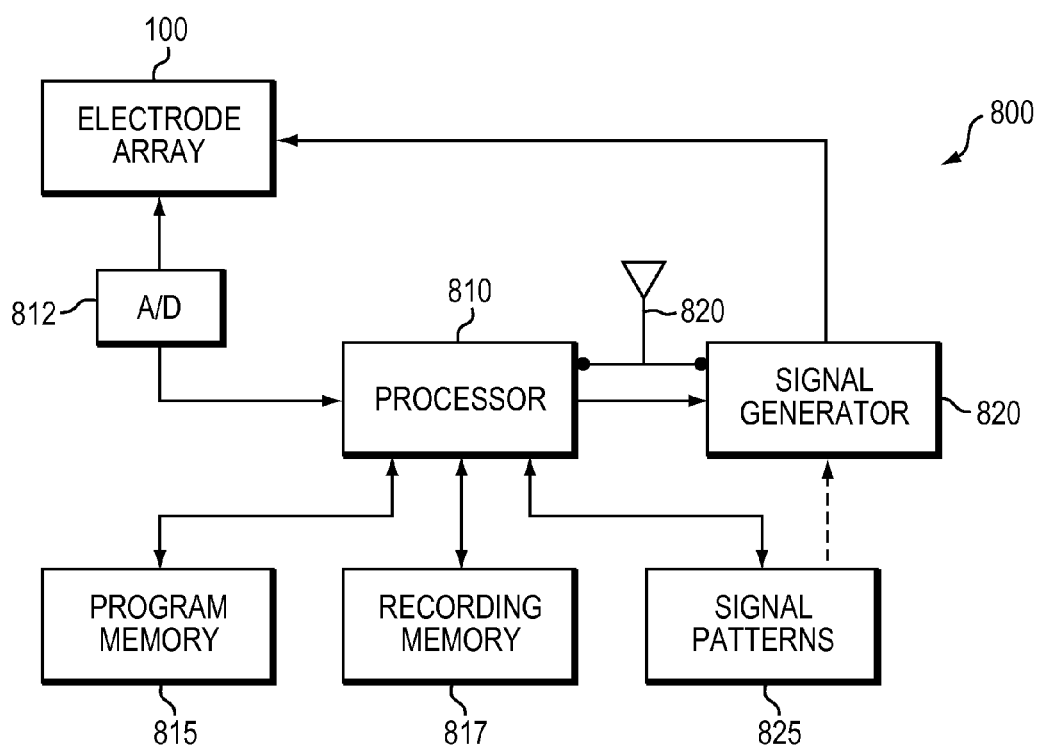

FIG. 8 schematically illustrates circuitry implementing the functions of an embodiment of the invention.

DETAILED DESCRIPTION

As used herein, the term "dura" refers to the fibrous membrane covering the brain and lining the inner surface of the skull; "electrocorticogram" (ECoG) refers to measurement of electrical brain activity from electrodes placed with the cranium and in close proximity to the cerebral cortex; "resection" means surgical removal of a part of the brain responsible for initiating or propagating seizure activity (and for purposes hereof, subpial transections are considered within the definition of resection); "subdural" refers to the volume within the cranium below the dura mater but above the arachnoid membrane of the meninges; "epileptogenic foci" refer to locations of epileptic abnormalities with the brain; and an "ASIC" means an application-specific integrated circuit, i.e., an electrical circuit device fabricated usually in silicon and designed for a specific application, or a general-purpose processor. The ASIC may be implemented in conjunction with, as appropriate, support circuitry to provide various functions, although some or all such functions can, in some embodiments, be internal to the ASIC. For ease of discussion, the ASIC or the general-purpose processor, and support circuitry, if any, are collectively referred to simply as the ASIC itself until more fully elaborated below.

Figure 1A:
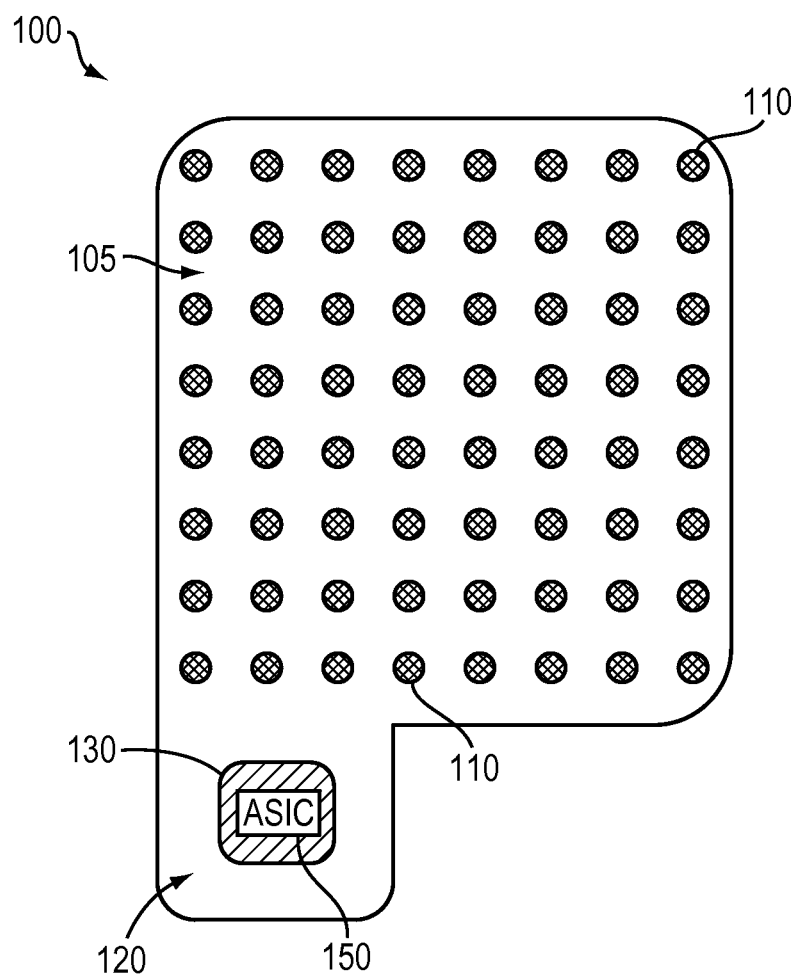
FIGS. 1A and 1B show plan (the brain-facing surface) and elevational views, respectively, of a wireless electrode array having 64 recording and stimulation electrodes in an 8×8 array and an encapsulated ASIC on a flexible polymer substrate.
Figure 1B:
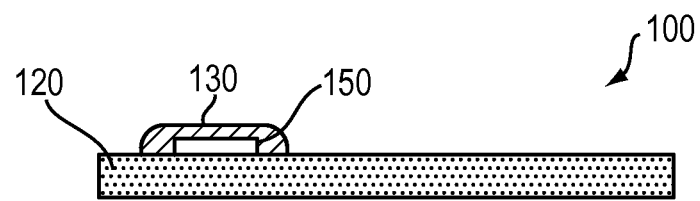

The plan and cross-sectional views of the brain-facing surface (105) of a wireless, subdural electrode array (100) for chronic recording and localization of, e.g., epileptogenic foci prior to resective surgery are shown in FIGS. 1A and 1B, respectively. The array (100) is typically formed of electrodes (110), which can record a voltage and can apply a stimulation voltage. Array (100) may be fabricated on a flexible polymer substrate (120) and an application-specific integrated circuit (ASIC) (150), which can provide functional control and data management, can also be mounted on substrate (120). The ASIC (150) and electrical connections with the substrate (120) are desirably protected by an encapsulating overlayer (130). Each individual electrode can communicate with the ASIC, i.e., send signals to the ASIC and receive signals from it. These communications may occur through metal interconnects (not shown) on the array.

Figure 2A:
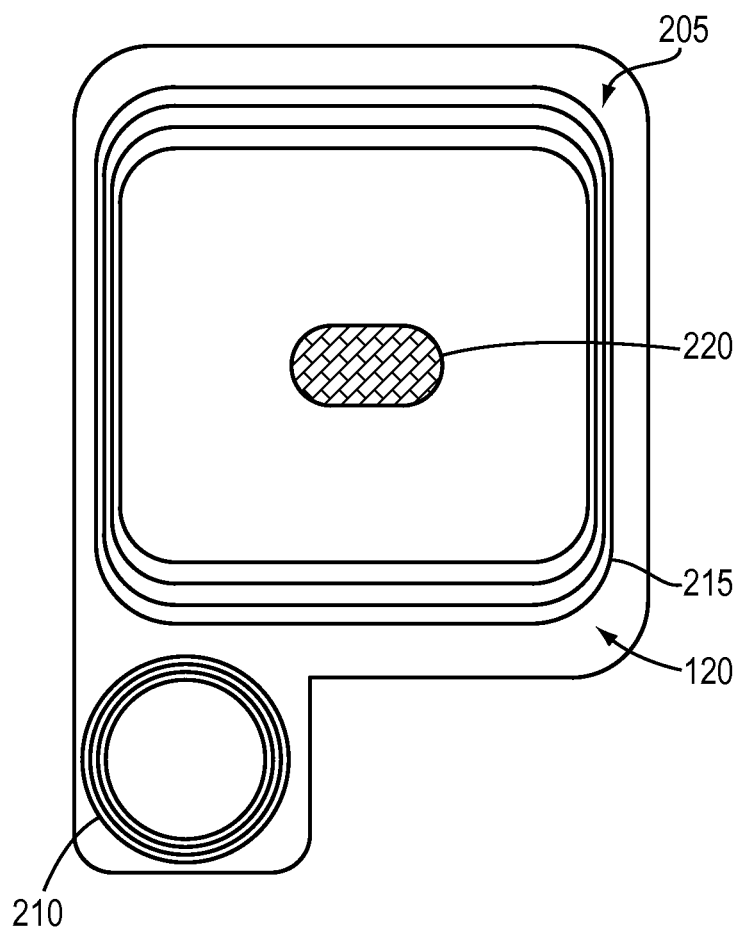
FIGS. 2A and 2B show plan (the dura-facing surface) and elevational views, respectively, of a wireless electrode array showing power and data coils, and a reference electrode for ECoG recordings, on a flexible polymer substrate.
Figure 2B:
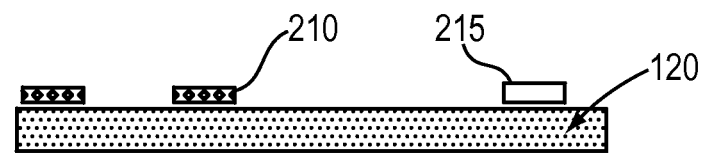

The dura-facing surface (205) of the array (100) of FIGS. 1A and 1B and a cross-sectional view of the dura-facing surface (205), according to one embodiment, are shown in FIGS. 2A and 2B, respectively. Mounted on the dura-facing surface (205) are two transcutaneous magnetic coupling coils—a data coil (210) for data transmission, and a power coil (215)—for receiving power to drive the ASIC. The dura-facing surface (205) of the array (100) also includes a reference electrode (220), which provides a reference voltage that can be used in recording the ECoG signals received from the array (100). As an external reference voltage source need not be used with the array (100) in this embodiment, it can be considered a self-contained array. The electrical connections (not shown) from the magnetic coupling coils, i.e., data coil (210) and power coil (215) and reference electrode (220), pass through the polymer substrate (120) to metal interconnects (not shown) on the brain-facing surface in order to connect the coupling coils and the reference electrode to the ASIC (150).

The array (100) of FIG. 1A shows 64 recording and stimulation electrodes (110), arranged in an 8×8 array. Array (100) can provide 64 channels of ECoG data, and can also supply electrical stimulation pulses between any two or more of the 64 electrodes on the brain-facing surface. It should be understood, however, that this is for illustrative purposes only, and applications involving more or fewer (e.g., as few as two) electrodes, other forms or structures of arranging these electrodes, and different numbers of channels of ECoG data are within the scope of the invention.

In an embodiment of the invention, the polymer substrate (120) is fabricated from a thin sheet of polyimide. A polyimide is suitable for thin-film fabrication using the well-known processes of photolithography and vacuum deposition to create metal interconnects (not shown) on the substrate that connect the ASIC (150) and electrodes (110). Although not essential, it is advantageous for fabrication by thin-film processing techniques to form the polyimide on a silicon wafer by spin-coating using a commercially available product such as HD-Microsystems PI-2660 or similar material. The polyimide substrate is desirably thin, preferably in the 5-50 µm range, although thicker substrates are contemplated when less flexibility is required. The metal interconnects are typically gold, although metals such as platinum, iridium, copper, and the like may be employed. The metal interconnects typically are also thin, preferably in the 0.2-5 µm range, although thinner and thicker interconnects are possible if the higher electrical resistance encountered with thinner interconnects and increased fabrication complexity of thicker interconnects are acceptable. A second polyimide layer may be applied over the metal interconnects to provide electrical insulation and protection from body fluids.

Figure 3A:
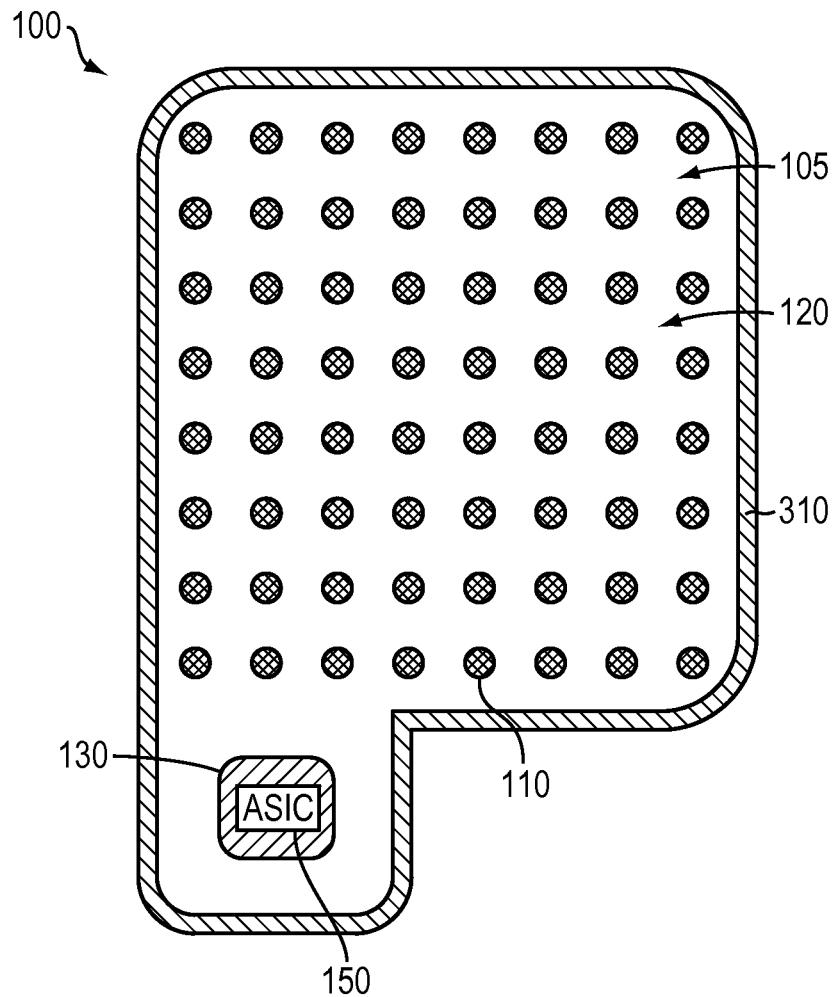
FIGS. 3A and 3B show plan (the brain-facing surface) and elevational views, respectively, of a wireless electrode array as shown in FIGS. 1A and 1B, including an elastomeric polymer coating on the dura-facing surface and edges of the flexible polymer substrate.
Figure 3B:
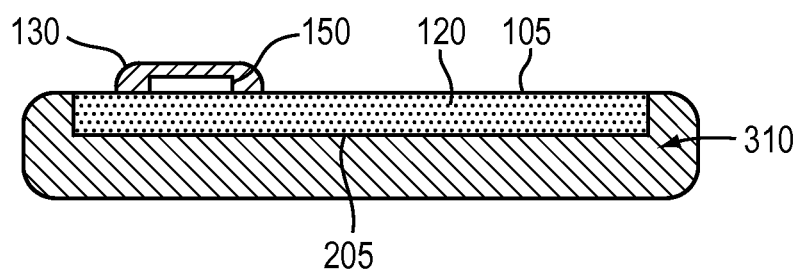

In a related embodiment, the polymer substrate (120) is partially coated with a second polymer having greater flexibility and, preferably, elastomeric properties. Plan and cross-sectional views of this embodiment are shown in FIGS. 3A and 3B, respectively. The elastomeric polymer (310) may be coated primarily on the dura-facing surface of the array. A second polymer layer (310) can aid in controlling the stiffness of the array so that it can be slid under the skull and into the subdural space from the edge of a craniotomy used to expose the patient's brain. The elastomer (310) also smooths the edges of the array (100), reducing the possibility that the sharp edges of the first polymer substrate (120) may cut or irritate tissue. The polymer of the second layer (310) is also selected for biocompatibility and to minimize tissue attachment that otherwise might make removal of the array from the patient at the end of the monitoring period difficult. Exemplary elastomers (310) include silicones and polyurethanes.

Figure 4:
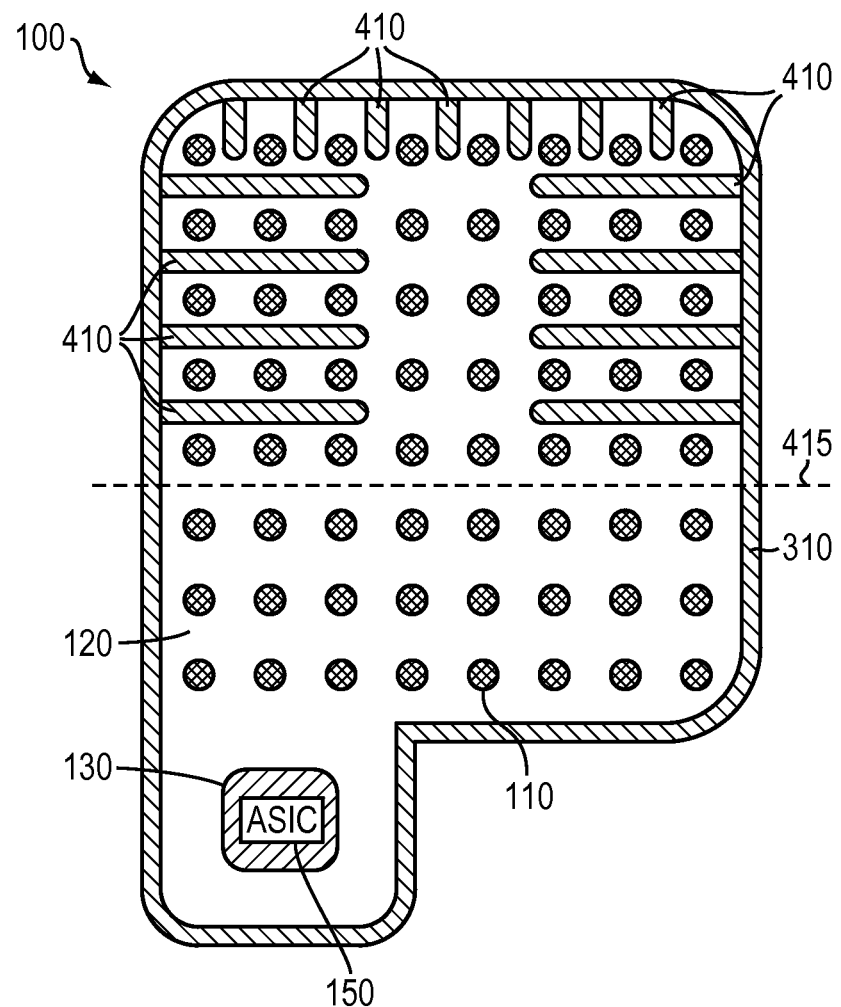
FIG. 4 shows the plan (the brain-facing surface) view of a wireless electrode array as shown in FIGS. 3A and 3B, including slits in the flexible polymer substrate.

In an embodiment of the invention that increases the flexibility of the subdural array to promote close apposition between the electrodes and the curved surface of the brain, a series of slits (410) are formed in the first polymer substrate (120), as shown in FIG. 4. Slits (410) are arranged geometrically to promote flexure in both parallel and perpendicular directions to the longitudinal axis (415) of array (100). In FIG. 4, the elastomeric polymer (310) is shown bridging the gaps created by the slits (410) in the first polymer substrate (120). It is equally possible to avoid bridging the gaps with the elastomeric polymer—i.e., having the slits (410) extend through elastomeric polymer (310) as well as substrate (120)—further enhancing the flexibility of the array.

In an embodiment of the invention that provides low-impedance recording and low polarization stimulation, the electrode sites on the wireless arrays are coated with platinum, porous platinum, high-surface-area titanium nitride, a conductive polymer, or iridium oxide. An exemplary conductive polymer is polyethylenedioxythiophene. In an embodiment particularly useful in connection with thin-film processing methods, the electrode sites are coated with a film of sputtered iridium oxide (SIROF). The maximum expected current in a biphasic stimulation pulse for cortical mapping is 20 mA delivered with a 0.2 ms/phase rectangular pulse. For a 3-mm diameter electrode, typical of wired subdural arrays presently in clinical use, the stimulation charge density is 58 $\mu C/cm^2$. This charge density is a small fraction of the charge-injection capacity of SIROF (>1000 $\mu C/cm^2$), and no significant polarization or dissolution of the SIROF will be encountered at this charge level. The charge density is, however, beyond the maximum capacity of stainless steel and some dissolution of platinum has been observed at these charge levels. The low polarization has the advantage of reducing the power and maximum voltage necessary to deliver the stimulation. The thickness of the SIROF is preferably between 0.1 $\mu m$ and 1 $\mu m$. Other forms of iridium oxide such as activated iridium oxide (AIROF) and electrodeposited iridium oxide (EIROF) may also be employed.

Figure 5:
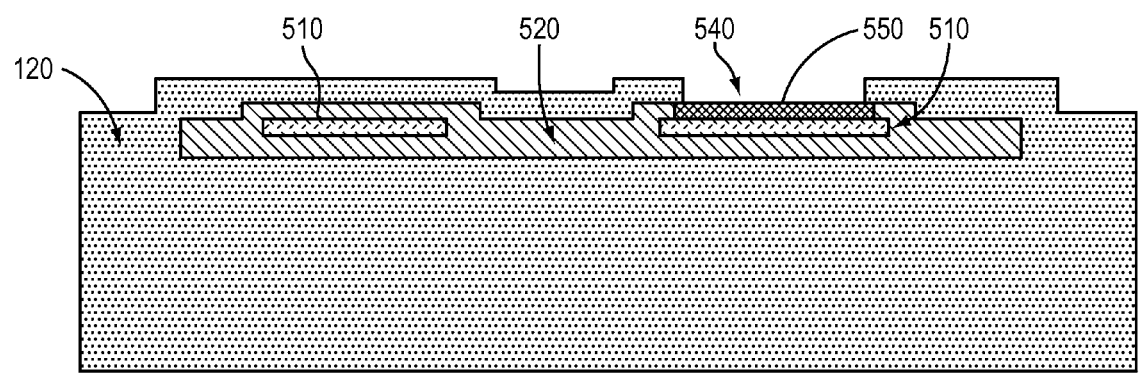
FIG. 5 is a schematic elevational view showing an exemplary use of amorphous silicon carbide (a-SiC) as a encapsulation layer and as an interlayer to promote adhesion at polymer-polymer and metal-polymer interfaces.

In an embodiment of the invention directed to wireless subdural arrays having improved durability in the body, and in particular improved adhesion at polymer-polymer and polymer-metal interfaces and improved encapsulation of the metal interconnects, one or more thin films of amorphous silicon carbide (a-SiC), alone or in combination with amorphous silicon oxycarbide, are deposited at the aforementioned interfaces. An exemplary use of a-SiC to encapsulate the metal interconnects on the polymer array is shown in FIG. 5. A metal interconnect (510) is circumferentially enclosed in a-SiC (520). The a-SiC (520) prevents reactive constituents of body fluids from undergoing damaging reactions at the surface of the metal interconnect (510) and also prevents diffusion of body fluid components along the interface between the metal interconnect (510) and the polymer substrate (120). The a-SiC (520) also extends under the metal interconnect (510) where the polymer (120) is removed to create a site (540) for an electrode for recording or stimulation. The electrode site (540) can be coated with a film of sputtered iridium oxide (SIROF) (550) to form the electrode. The a-SiC (520) provides a strong adhesive bond between the metal interconnect (510) and the polymer substrate (120) and prevents delamination of the metal from the polymer at the electrode site (540) during electrical stimulation of tissue by charge-injection through the SIROF electrode coating (550).

In an embodiment of the invention, shown in FIG. 6, the surgeon, at the time of array implantation, can remove selected electrodes from the array by physically trimming an unwanted portion of the array. The metal interconnects (610) that connect the electrodes (615) to the ASIC (not shown) are patterned and routed on the polymer substrate (120) so as to allow removal of some peripheral electrodes without interrupting the connection between the ASIC and remaining electrodes. A surgeon may choose to remove, for example, three electrodes (615) from a corner (620) of the array (100). A pair of cuts (630) to remove these electrodes can be made by the surgeon using a scissors or another appropriate tool. Metal interconnects (610) are severed by the cuts (630). All other metal interconnects (640) on the array maintain connection between the electrodes (645), other sites (not shown), and the ASIC. FIG. 6 is illustrative only and those skilled in the art of thin-film fabrication and photolithography will appreciate that the metal interconnects (610, 640) may have a range of sizes and geometries.

Also shown in FIG. 6, features may be incorporated to provide a convenient indication to a surgeon where cuts may be made in the array to remove unwanted electrodes. In this embodiment, a plurality of slits (660) are located so that their longitudinal axes (665) define both the locations at which and the directions along which the surgeon may cut. In the illustrated embodiment, the surgeon can make the cuts in the elastomer polymer (310). In this way, the surgeon avoids exposing what might otherwise by hard or sharp edges of the polymer substrate (120).

In some embodiments of an array (100) according to the present invention, the photolithographically patterned metal interconnects (610, 640) can be too small to be readily observed by a surgeon. Without an indication of a permissible cut location, as illustrated in FIG. 6, a surgeon may accidentally cut metal interconnects (640) needed by the electrodes (645) and the ASIC to communicate with one another, rendering such communication infeasible.

In an embodiment of the invention, more than one electrode array can be implanted inside a patient's brain. The ASICs of each array can be designed to permit concurrent operation and ECoG recording from multiple arrays. The ASICs record signals from all electrode channels, each ASIC sampling and transmitting ECoG waveforms corresponding to the array on which the ASIC resides, at a rate of, e.g., at least 100 samples per second and preferably over 200 samples per second.

In an embodiment of the invention that provides for implantation at confined sites within the subdural space, between hemispheres of the brain, or within a sulcus of the brain, differently shaped arrays with different numbers of electrodes can be deployed. There is no particular restriction on the shape and number of electrodes on an array, and exemplary wireless array designs are shown in FIG. 7. The exemplary designs include an 8×8 grid (710), a temporal lobe subdural grid with 48 electrodes (715), a linear 1×8 array with eight electrodes (720), a linear 2×8 array with 16 electrodes (725), and a multi-direction linear array with 16 electrodes (730). For multi-directional arrays, designs with different numbers of arms extending in various "star-burst" geometries may be employed.

A method in accordance with the invention improves diagnostic localization information from ECoG waveform monitoring prior to epilepsy surgery. In accordance with the method, one or a plurality of wireless arrays is implanted subdurally in a patient. The patient is maintained on a normal regimen of anti-seizure medication. Periodically, ECoG waveforms are wirelessly measured (using an electrode array as described above) for a period of time sufficient to include habitual seizure activity. These waveforms are analyzed, in accordance with techniques well-characterized in the art, to localize pharmacologically intractable epileptogenic foci. In addition, at one or more times during the recording period, cortical mapping studies may be conducted using wireless electrical stimulation through one or more of the recording electrode sites on the wireless array.

The functional modules of a representative implementation 800 of the invention are shown in FIG. 8. As noted above, any or all of these modules may be included within the physical package of ASIC (150) or may instead be variously deployed as separate onboard support circuitry. A processor (810) receives signals from electrode array (100), representing sensed brain voltages, via an analog-to-digital converter (812). The operations performed by processor (810) on these digitized signals are determined by the contents of a program memory (815). The program memory may be a non-volatile, programmable storage device such as, for example, Flash memory. The processor (810) may be programmed using any suitable programming language or languages (e.g., C, C++, C#, Java, Visual Basic, LISP, BASIC, PERL, assembly, etc.), and, as described below, the contents of program memory (815) may be modified externally while the device is implanted.

Depending on the program instructions, processor (810) may store the digitized sensed signals, or portion thereof, from array (100) in a recording memory (or memory partition) (817). For example, recording memory (817) may be configured as a rolling buffer, the contents of which are periodically transmitted externally via a signal generator (820) to an external reader. Alternatively, or at different times, the processor (810) (in accordance with its program instructions) may cause the digitized signals to be transmitted immediately via signal generator (820). For example, the processor (810) may analyze the incoming brain signals and cause transmission thereof only during the detected onset of a clinically significant electrical brain event. The signal generator (820) transmits data wirelessly via an antenna (822), which may be, for example, the data coil (210).

The processor (810) receives a reference voltage from the reference electrode in array (100), computing ECoG data as a difference between the reference electrode voltage and the voltage sensed by any of the sensing electrodes in the array (100). Alternatively, the data may be transmitted without analysis, so that the external reader computes ECoG data. The processor (810) may modify the data or its format, i.e., arrange it into groups of different sizes.

The wirelessly transmitted data may be modified or unmodified. The antenna (822) can also receive commands and/or data wirelessly, as electrical signals, from an external source. These signals can, for example, command a stimulus voltage to be applied by one or more of electrodes in the array (100). The stimulus voltages to be applied by different electrodes can be identical or different, according to the commands received. The commands may also direct which electrodes may apply a stimulus voltage.

Processor (810) can be programmable (as well as directly commanded) via the wireless electromagnetic link with a source outside the patient's brain, e.g., by facilitating augmentation or alteration of the programming instructions in program memory (815). Moreover, a signal-pattern memory 825 may receive, from the external source, a pattern of signals to be applied to the brain via signal generator (820) and electrode array (100). Each signal pattern is stored and applied, either immediately under the command of the external source, or in accordance with program instructions in program memory (815) (which, once again, may themselves originate with the external source).

Programmable operation of the processor (810) can provide for autonomous periodic sensing and transmission of ECoG waveforms in a manner predetermined by the clinician. For example, a clinician can program selection of various of the electrodes in array (110) from which voltages are to be sensed and the time (or a series of times) at which voltages are to be sensed from each selected electrode. A clinician can also select electrodes to provide a stimulus, the stimulus voltage, its frequency, duration, and the time(s) at which it is to be applied. This information is stored in memories (815, 825) and/or at a source outside the patient's brain. If a clinician so desires, a stored program can be revised and re-transmitted.

Although the present invention has been described with reference to specific details, it is not intended that such details should be regarded as limitations upon the scope of the invention, except as and to the extent that they are included in the accompanying claims.

What is claimed is:

1. A medical device for recording and stimulating brain activity at a site of device implantation, comprising: an implantable flexible substrate having a dura-facing side and an opposing brain-facing side; an array of electrodes disposed on said brain-facing side and adapted for sensing electrical signals from a subject's brain; a reference electrode mounted on said dura-facing side, wherein said reference electrode is physically separated from the subject's brain by the flexible substrate and adapted to provide a reference voltage; implantable control circuitry in communication with the brain-facing electrodes and said dura-facing reference electrode; implantable wireless transmission circuitry connected to the control circuitry and adapted to transmit digital data derived from said sensed brain electrical signals to receiving circuitry external to the site of device implantation; and implantable wireless receiver circuitry for receiving wireless commands transmitted from a site external to the site of device implantation, wherein said implantable control circuitry provides an electrical stimulus to the subject's brain via at least two of said brain-facing electrodes and records sensed electrical signals based on said reference voltage and said sensed electrical signals.

2. The medical device of claim 1 wherein the transmission circuitry includes means facilitating magnetic inductive coupling.

3. The medical device of claim 2 wherein the receiver circuitry includes means facilitating magnetic inductive coupling.

4. The medical device of claim 3 wherein means facilitating magnetic inductive coupling comprises a single metal coil.

5. The medical device of claim 1 wherein said flexible substrate comprises one or more layers of flexible polymer.

6. The medical device of claim 5 wherein the flexible substrate comprises a plurality of layers, and further comprising at least one film that itself comprises at least one of (a) amorphous silicon carbide or (b) amorphous silicon oxycarbide.

7. The medical device of claim 6 wherein the film is disposed between a layer of the flexible substrate and the brain-facing electrodes.

8. The medical device of claim 6 wherein the film is disposed between two of the layers of the flexible substrate.

9. The medical device of claim 5 wherein the flexible substrate comprises slits facilitating flexure thereof.

10. The medical device of claim 1 wherein the brain-facing electrodes are coated with iridium oxide.

11. The medical device of claim 1 further comprising metal conductors disposed on the flexible substrate and connecting the implantable control circuitry and the brain-facing electrodes.

12. The medical device of claim 1 wherein at least some of the brain-facing electrodes are physically removable without disrupting connections between the remaining brain-facing electrodes and the implantable control circuitry.

13. The medical device of claim 1 further comprising a program memory modifiable in response to signals wirelessly received by the receiver circuitry, wherein the implantable control circuitry is responsive to the program memory.

14. The medical device of claim 1 further comprising a pattern memory, operatively coupled to the implantable control circuitry, for storing signal patterns to be applied to the array of electrodes by the implantable control circuitry.

15. The medical device of claim 14 wherein the pattern memory is externally modifiable in response to signals wirelessly received by the implantable receiver circuitry.

16. A method of brain monitoring and treatment, the method comprising the steps of: subdurally implanting a device comprising a flexible substrate having a dura-facing side and an opposing brain-facing side, wherein the flexible substrate comprises an array of electrodes positioned on the brain-facing side for sensing signals generated by the subject's brain or applying an electrical stimulus to the subject's brain and a reference electrode positioned on the dura-facing side wherein said reference electrode is physically separated from the subject's brain by the flexible substrate and is adapted to provide a reference voltage; recording sensed electrical signals based on said reference voltage and said sensed electrical signals; wirelessly transmitting digital data derived from the brain signals sensed by electrodes within said array of electrodes; and transmitting wireless commands to cause a delivery of an electrical stimulus to the patient's brain via at least two electrodes within said array of electrodes.

17. The method of claim 16 wherein the wireless commands specify parameters comprising one or more selected electrodes of the array of electrodes, a stimulus magnitude for each of the selected electrodes, a stimulus frequency for each of the selected electrodes, and a stimulus duration for each of the selected electrodes, wherein each of the selected electrodes are energized in accordance with the parameters.

* * * * *